(12) United States Patent
Jones et al.

(10) Patent No.: US 6,990,975 B1
(45) Date of Patent: Jan. 31, 2006

(54) MEDICAMENT DELIVERY SYSTEM (75) Inventors: Anthony Patrick Jones, Ware (GB); Gregor John McLennan Anderson, Ware (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,830

(22) PCT Filed: Feb. 23, 2000

(86) PCT No.: PCT/EP00/01443

§ 371 (c)(1),
(2), (4) Date: Sep. 24, 2001

(87) PCT Pub. No.: WO00/53247

PCT Pub. Date: Sep. 14, 2000

(30) Foreign Application Priority Data

| Mar. 6, 1999 | (GB) | ................................... 9905134 |
| Jul. 27, 1999 | (GB) | ................................... 9917470 |

(51) Int. Cl.
*A61M 11/00* (2006.01)
*A61M 15/00* (2006.01)

(52) U.S. Cl. .......................... 128/200.23; 128/200.14; 128/203.15

(58) Field of Classification Search .......... 128/200.14, 128/200.21, 200.23, 202.12, 203.13, 203.14, 128/203.25, 203.15, 205.23
See application file for complete search history.

(56) References Cited

U.S. PATENT DOCUMENTS

| 3,695,263 | A |   | 10/1972 | Kipling |
| 4,176,663 | A |   | 12/1979 | Hewlett |
| 4,495,944 | A | * | 1/1985 | Brisson et al. ......... 128/203.12 |
| 4,533,346 | A | * | 8/1985 | Cosgrove et al. ............. 604/66 |
| 4,648,393 | A | * | 3/1987 | Landis et al. .......... 128/200.23 |
| 4,706,664 | A | * | 11/1987 | Snook et al. .......... 128/204.23 |
| 4,829,998 | A | * | 5/1989 | Jackson ................. 128/203.12 |
| 4,932,402 | A | * | 6/1990 | Snook et al. .......... 128/204.23 |
| 4,938,212 | A | * | 7/1990 | Snook et al. .......... 128/205.24 |
| 4,984,158 | A | * | 1/1991 | Hillsman ................ 364/413.04 |
| 5,080,093 | A | * | 1/1992 | Raabe et al. .......... 128/203.12 |
| 5,167,506 | A | * | 12/1992 | Kilis et al. .................. 434/262 |
| 5,284,133 | A | * | 2/1994 | Burns et al. ........... 128/200.23 |
| 5,310,092 | A | * | 5/1994 | Targell ........................ 222/167 |
| 5,322,057 | A | * | 6/1994 | Raabe et al. ........... 128/203.12 |
| 5,333,106 | A | * | 7/1994 | Lanpher et al. ........ 364/413.01 |
| 5,349,946 | A | * | 9/1994 | McComb ............... 128/203.17 |
| 5,363,842 | A | * | 11/1994 | Mishelevich et al. .. 128/200.14 |
| 5,368,015 | A | * | 11/1994 | Wilk .......................... 600/104 |
| 5,404,871 | A | * | 4/1995 | Goodman ............... 128/200.23 |
| 5,469,750 | A |   | 11/1995 | Lloyd et al. |
| 5,479,920 | A | * | 1/1996 | Piper et al. ............. 128/204.23 |
| 5,487,378 | A | * | 1/1996 | Robertson et al. ..... 128/200.16 |

(Continued)

FOREIGN PATENT DOCUMENTS

WO    WO9212750 A    8/1992

(Continued)

*Primary Examiner*—Teena Mitchell
(74) *Attorney, Agent, or Firm*—James F. Riek (57) ABSTRACT

There is provided a system for the delivery of inhalable medicament comprising a monitor (40) for monitoring the breath cycle of a patient, a medicament container (2) having a release mechanism (4, 5) for releasing inhalable medicament therefrom, and an actuator (50) for actuating said release mechanism, the actuator (50) being actuable in response to a signal from the monitor (40). The monitor (40) provides the signal at a trigger point which is coupled to the end of the exhalation part of the breath cycle.

38 Claims, 5 Drawing Sheets

U.S. PATENT DOCUMENTS

| | | | |
|---|---|---|---|
| 5,497,764 A * | 3/1996 | Ritson et al. | 128/200.14 |
| 5,520,166 A * | 5/1996 | Ritson et al. | 128/200.14 |
| 5,522,378 A * | 6/1996 | Ritson et al. | 128/200.14 |
| 5,608,647 A | 3/1997 | Rubsamen et al. | |
| 5,694,919 A * | 12/1997 | Rubsamen et al. | 128/200.14 |
| 5,743,252 A * | 4/1998 | Rubsamen et al. | 128/200.14 |
| 5,755,218 A * | 5/1998 | Johansson et al. | 128/200.14 |
| 5,809,997 A * | 9/1998 | Wolf | 128/200.23 |
| 5,813,397 A * | 9/1998 | Goodman et al. | 128/200.14 |
| 5,826,570 A * | 10/1998 | Goodman et al. | 128/200.14 |
| 5,842,467 A | 12/1998 | Greco | |
| 6,024,704 A * | 2/2000 | Meador et al. | 600/486 |
| 6,234,973 B1 * | 5/2001 | Meador et al. | 600/486 |
| 6,260,549 B1 * | 7/2001 | Sosiak | 128/200.23 |
| 6,584,972 B2 * | 7/2003 | McPhee | 128/203.17 |
| 6,694,974 B1 * | 2/2004 | George-Gradon et al. | 128/203.17 |

FOREIGN PATENT DOCUMENTS

| | | |
|---|---|---|
| WO | WO99 04841 A | 2/1999 |

\* cited by examiner

FIG. 1

(PRIOR ART)

MEDICAMENT DELIVERY SYSTEM

CROSS-REFERENCE TO RELATED APPLICATIONS

This application is filed pursuant to 35 U.S.C. §371 as a United States National Phase Application of International Application No. PCT/EP00/01443 filed 23 Feb. 2000, which claims priority from GB9905134.4 filed 6 Mar. 1999 and GB9917470.8 filed 27 Jul. 1999.

BACKGROUND OF THE INVENTION

1. Field of the Invention

The present invention relates to a system for the delivery of inhalable medicament to a patient at a preset point in the breathing pattern of the patient. In particular, the invention relates to metered dose inhalers by means of which medicament may be delivered in metered doses.

2. Description of Related Art

It is well known to treat patients with medicaments contained in an aerosol, for example, in the treatment of respiratory disorders. It is also known to use for such treatment, medicaments which are contained in an aerosol and are administered to a patient by means of an inhalation device comprising a tubular housing or sleeve in which the aerosol container is located and an outlet tube leading out of the tubular housing. The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the patient then holds the housing in a more or less upright condition and the mouthpiece or nozzle of the inhalation device is placed in the mouth or nose of the patient. The aerosol container is pressed towards the support to dispense a dose of medicament from the container which is then inhaled by the patent.

It may be understood that effective delivery of medicament to the patient using an inhalation device as described above is to an extent dependent on the patient's ability to co-ordinate the actuation of the device (e.g. firing of the aerosol) with the taking of a sufficiently strong inward breath. For some patients the required co-ordination can present difficulties. Other patients, particularly those having severe respiratory problems, find it difficult to produce a reliable inward breath. Both of these sets of patients run the risk that they do not receive the appropriate dose of medicament.

Breath-actuable or breath-assisted inhalation devices have been developed to address the needs of patients having poor co-ordination skills and/or unreliable breath capability. Such devices typically have a breath trigger mechanism which triggers release of medicament in response to the inward breath of a patient.

One problem inherent with such breath-triggered devices is that a certain amount of the inward breath is used up before the trigger is activated. The full inward breath is thus, not available for inhalation of medicament. Further, that initial part of the inward breath which is 'lost' prior to release of the medicament is a relatively strong and inhalation-effective portion of the full inward breath. Where the patient has poor breath capacity the loss of this portion of the inward breath may significantly compromise the amount of medicament which is deliverable to the lungs.

Another problem with such breath-triggered devices is that the medicament may not be released at the optimum point in the breath cycle.

The Applicants have now found that enhanced delivery of medicament is achievable by use of a system in which the breathing pattern of a patient is monitored and drug release is coordinated with a preset point in the breathing pattern. This preset point is selected to optimise the delivery of drug to the lung. It has been found to be particularly advantageous if the preset point is defined relative to, or indeed to coincide with, the end of the exhalation part of the breath cycle.

The Applicants have also now appreciated that at the end of the exhalation part of the breath cycle, the patient's mouth cavity is typically at rest which allows it to act as a natural 'spacer' element, thereby assisting with dispersal of the delivered medicament. There is thus, potentially less need for the use of a separate mechanical spacer element as is commonly used in conjunction with the mouthpiece of conventional inhalation devices.

BRIEF SUMMARY OF THE INVENTION

According to one aspect of the present invention there is provided a system for the delivery of inhalable medicament comprising a monitor for monitoring the breath cycle of a patient; a medicament container having a release mechanism for releasing inhalable medicament therefrom; and an actuator for actuating said release mechanism, said actuator being actuable in response to a signal from said monitor. The monitor provides said signal at a trigger point which is coupled to the end of the exhalation part of the breath cycle.

By release mechanism herein it is meant any mechanism which enables release of medicament from the container. The release may be active in the sense that medicament is actively dispensed from the container (e.g. by the propellant-driven firing from an MDI aerosol container) or the release may be passive in the sense that medicament is merely made available for release (e.g. by removing a cover from a dry powder container) when the release mechanism is actuated.

By monitor herein it is meant any suitable means for monitoring, measuring, tracking or indicating the breath cycle of a patient including monitors employing one or more sensors. Suitable sensors include mechanical sensors such as those employing vanes or sails which are movable in response to airflow.

Preferably, the monitor comprises one or more sensors for sensing the pressure profile associated with the breath cycle. Pressure transducers are suitable sensors of this type.

Preferably, the monitor comprises one or more sensors for sensing the airflow profile associated with the breath cycle. Sprung vane sensors and sensors including anemometers are suitable sensors of this type.

Preferably, the monitor comprises one or more sensors for sensing the temperature profile associated with the breath cycle. The temperature of the inhaled and exhaled part of the breath cycle varies and may, thus, be used as a measurement tool.

Preferably, the monitor comprises one or more sensors for sensing the moisture profile associated with the breath cycle. The moisture content of the inhaled and exhaled part of the breath cycle varies and this also may be used as a measurement tool.

Preferably, the monitor comprises one or more sensors for sensing the chemical profile, particularly the oxygen or carbon dioxide profile, associated with the breath cycle. The chemical profile of the inhaled and exhaled part of the breath cycle varies and this further may be used as a measurement tool.

Preferably, the trigger point corresponds to the point at which the lungs of the patient are most empty.

Preferably, the monitor is connectable to an electronic information processor. The connection may be direct or via any suitable mechanical or electronic transfer means.

Preferably, the electronic information processor includes an active memory for storing information about the breath cycle.

Suitably, the electronic information processor includes a predictive algorithm or look-up table for predicting the optimum trigger point. For example, a real-time analysis of the patient waveform may be made and the optimum trigger point derived by reference to that analysed waveform.

Suitably, the electronic information processor includes a second predictive algorithm or look-up table for predicting the optimum amount of medicament to release. Suitably, the electronic information processor includes a dose memory for storing information about earlier delivered doses and reference is made to the dose memory in predicting the optimum amount of medicament to release.

Suitably, the system additionally comprises a display for displaying information about the optimum amount of medicament to release.

Suitably, the system additionally comprises a selector for selecting the amount of medicament to release.

In one aspect, the selector is manually operable.

In another aspect, the selector is automatically operable in response to a signal from the electronic information processor.

Suitably, the selector comprises a timing mechanism for varying the time interval of actuation of the actuator.

Suitably, the selector comprises a metering mechanism between the container and the release mechanism for metering a variable quantity of medicament for release.

Suitably, the selector comprises a multiple-fire mechanism for multiple actuation of the actuator, wherein each actuation releases a portion of the optimum amount of medicament. Successive actuations may be pulsed, for example such that the time intervals between actuations may be based on arithmetic or geometric progressions.

In one preferred aspect, the medicament container is an aerosol container and said release mechanism is an aerosol valve. Preferably, the aerosol valve includes a metering chamber for metering the release of medicament. More preferably, the metering chamber is of variable volume. The volume of the metering chamber may be for example, be varied to provide the optimum amount of medicament for release. In one preferred aspect, the volume of the metering chamber is variable automatically in response to a dosing signal sent from the electronic information processor.

Various types of variable volume metering chambers are envisaged. Suitable chambers comprise a fixed volume chamber whose metering volume is variable by insertion of a plunger or piston. The piston or plunger may have a fixed form or alternatively may comprises an element of variable shape and volume such as an inflatable balloon. Other suitable chambers comprise a chamber which is expandable because it is formed from a flexible/expandable material. Further suitable chambers have telescopic or concertina arrangements to allow for mechanical expansion of the metering volume.

In another preferred aspect, the medicament container is a dry-powder container or a liquid container, that is to say a container respectively suitable for containing medicament in dry-powder or liquid form.

Preferably, the actuator comprises an energy store for storing energy which energy is releasable to activate the release mechanism of the medicament container. The energy store comprises in preferred aspects, a biasable resilient member such as a spring, a source of compressed fluid such as a canister of compressed gas (e.g. carbon dioxide or air), or a voltaic cell or battery of voltaic cells. Chemical energy sources are also suitable and might include chemical propellant or ignition mixtures. Other sources might include physical explosives such as liquefied or solidified gas in a canister which burst when heated or exposed to the atmosphere.

Preferably, the system additionally comprises a safety mechanism to prevent unintended multiple actuations of the actuator. The patient is thereby protected from inadvertently receiving multiple doses of medicament in a situation where they take a number of short rapid breaths. More preferably, the safety mechanism imposes a time delay between successive actuations of the actuator. The time delay is typically of the order of from three to thirty seconds.

An actuation counter which can be mechanical or electronic may be provided to the system.

A medicament release counter, such as a dose counter, may be provided to the system. This may be mechanical or electronic. The counter may be coupled to a visual display to provide feedback to the patient as to amount of drug released or remaining in the container.

A manual override can be provided to the system for use in the event of emergency or system failure.

According to another aspect of the present invention there is provided an inhalation device for the delivery of inhalable medicament comprising a housing and a system as described above. Suitable housings typically comprise a cavity for receipt of the medicament container and an opening in the form of a mouthpiece or nozzle through which the medicament is delivered to the patient.

According to a further aspect of the present invention there is provided a method for the delivery of inhalable medicament to a patient comprising (i) monitoring the breath cycle of a patient by use of a monitor;

(ii) at a trigger point, sending an actuation signal from said monitor to an actuator;

(iii) on receipt of said actuation signal by said actuator, actuating the release of inhalable medicament to the patient, The trigger point is coupled to the end of the exhalation part of the breath cycle.

In step (i) a real-time analysis of the patient waveform may be made and comparison made with a medically acceptable waveform. Steps (i) to (iii) can then repeated until the patent waveform sufficiently matches the medically acceptable waveform.

Preferably, the method comprises (i) monitoring a plurality of breath cycles of a patient by use of a monitor, (ii) analysing said plurality of breath cycles to define an averaged breath cycle for the patient;

(iii) predicting a trigger point from said averaged breath cycle, the trigger point being coupled to the end of the exhalation part of the averaged breath cycle;

(iv) monitoring a further breath cycle and at said predicted trigger point sending an actuation signal from said monitor to an actuator;

(v) on receipt of said actuation signal by said actuator, actuating the release of inhalable medicament to the patient.

BRIEF DESCRIPTION OF THE SEVERAL VIEWS OF THE DRAWINGS

A system according to the invention will now be described with reference to the accompanying drawings in which.

DETAILED DESCRIPTION OF THE INVENTION

Figure 1:
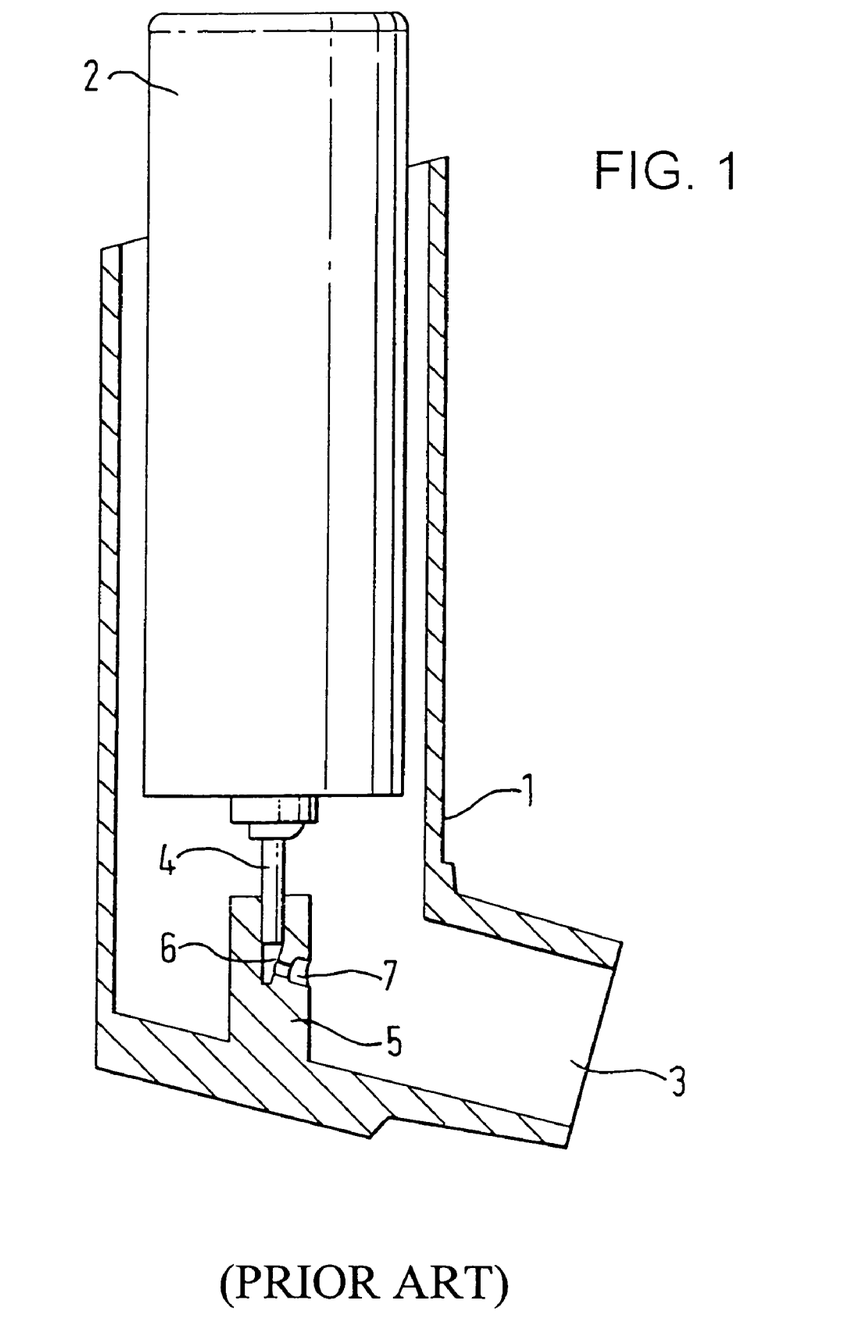
FIG. 1. is a sectional view of a standard metered dose inhaler.

The standard metered dose inhaler shown in FIG. 1 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril.

The aerosol container 2 has an outlet valve stem 4 at one end. This valve member can be depressed to release a measured dose from the aerosol container or, alternatively, the valve stem 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the container 2 spaced from the internal surface of the housing 1. A support 5 is provided at the lower end of the housing 1 and has a passage 6 in which the valve stem 4 of the aerosol container 2 can be located and supported. A second passage 7 is provided in the support 5 and is directed towards the interior of the outlet 3.

Thus, when the parts are in the positions shown in FIG. 1, the protruding portion of the aerosol container 2 can be depressed to move the container relative to the valve stem 4 to open the valve and a dose of medicament contained in the aerosol will be discharged through the passage 7 and into the outlet 3 from which it can be inhaled by a patient. One dose will be released from the aerosol container each time it is fully depressed.

Figure 2:
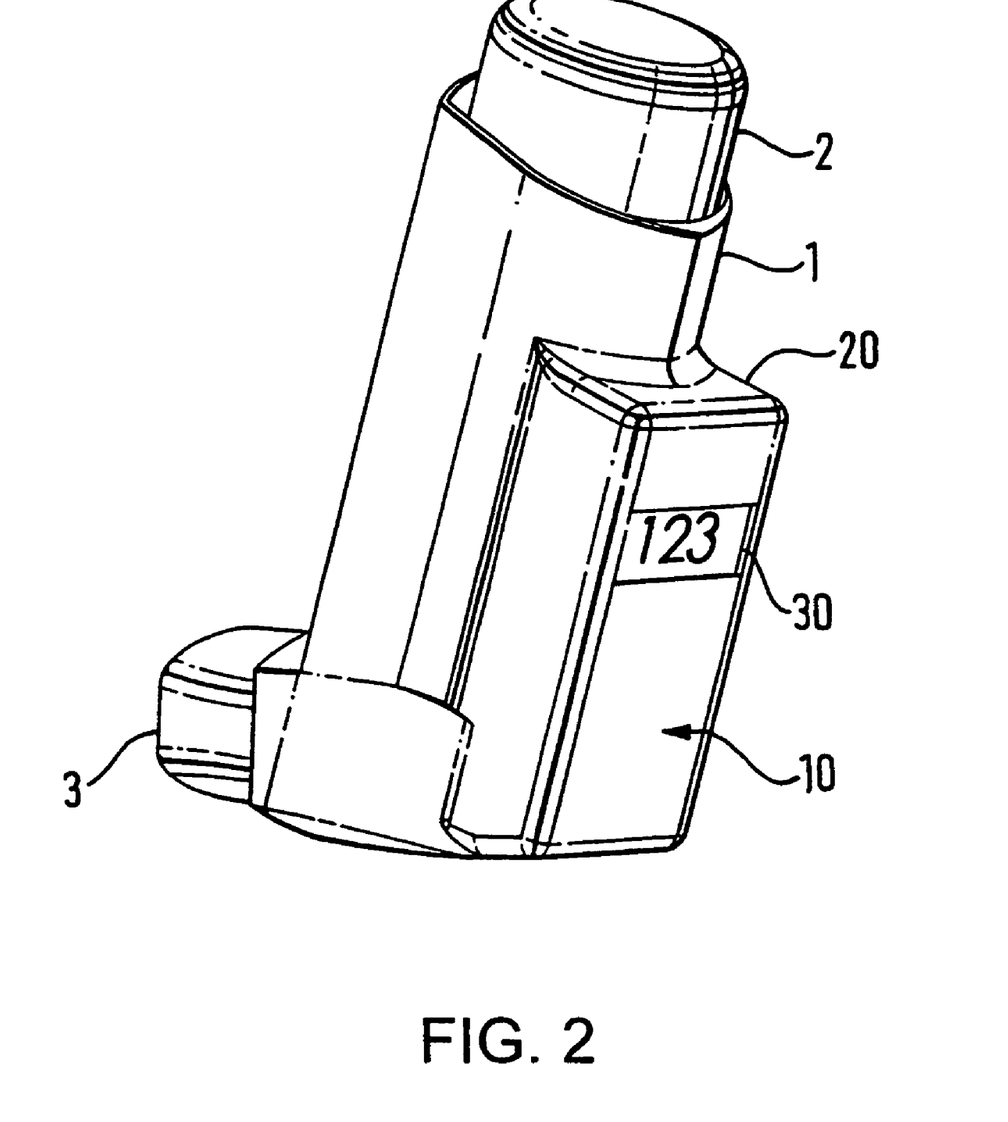
FIG. 2. is a perspective view of an inhalation device in accord with the present invention.

FIG. 2. shows a metered dose inhaler of the general type illustrated in FIG. 1. which includes an electronic device for monitoring the breath cycle of a patient. The device comprises housing 10 within which an electronic information processor 20 is housed. The electronic information processor 20 is connected to a sensor (not visible) for sensing the breathing pattern of the patient and an actuator (not visible) for actuating the release of aerosol from the container 2.

Visual display monitor 30 allows for display of information relating to doses dispensed from the container 2.

Figure 3:
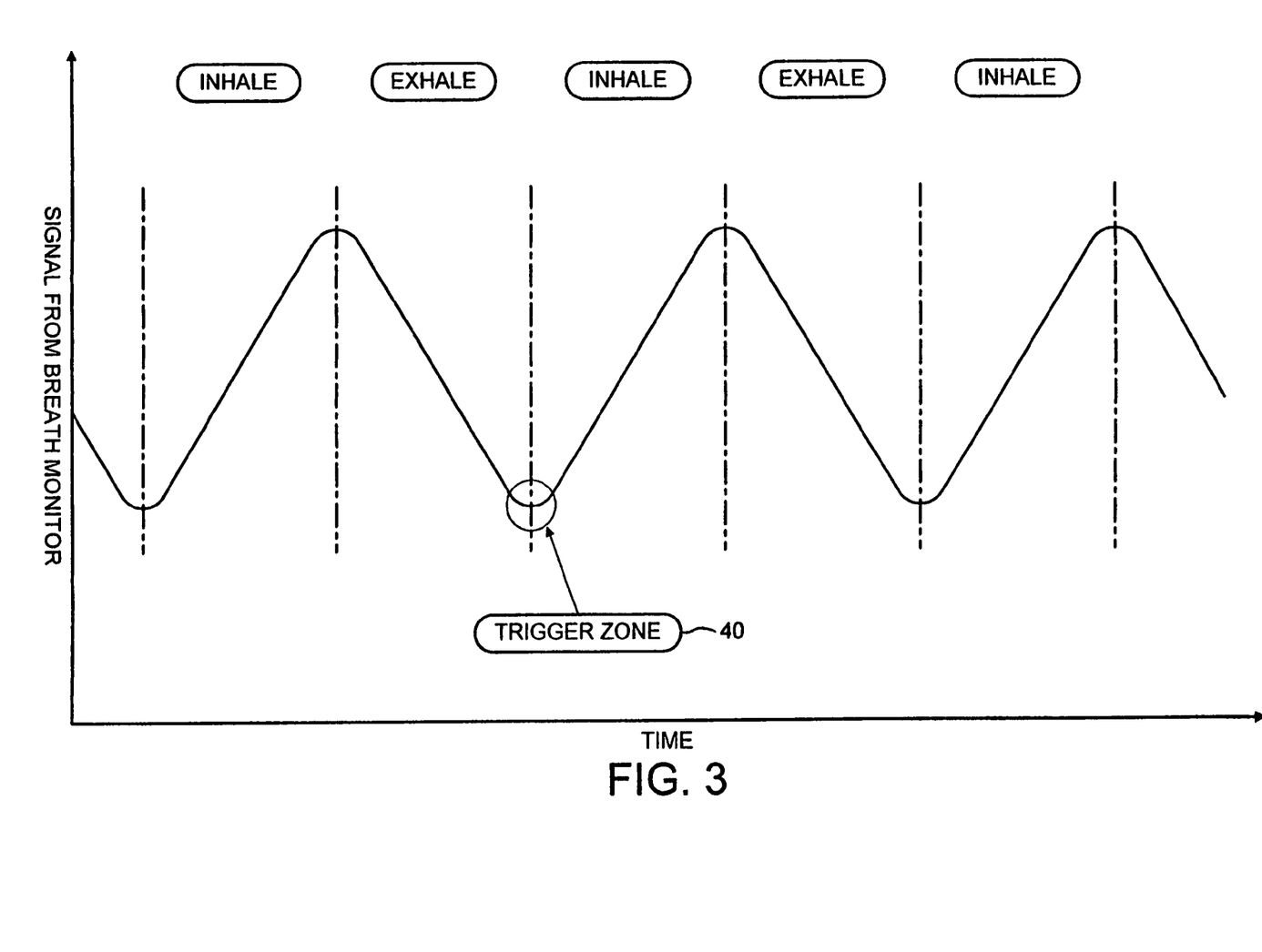
FIG. 3. is a graphical representation of a patient breathing pattern.

FIG. 3. depicts the breathing pattern of a patient in simplified graphical form wherein the vertical axis represents the volume of air in the lungs and the horizontal axis represents time. A trigger zone 40 is indicated which corresponds to the portion in the breath cycle at which the lungs are at their most empty.

Figure 4:
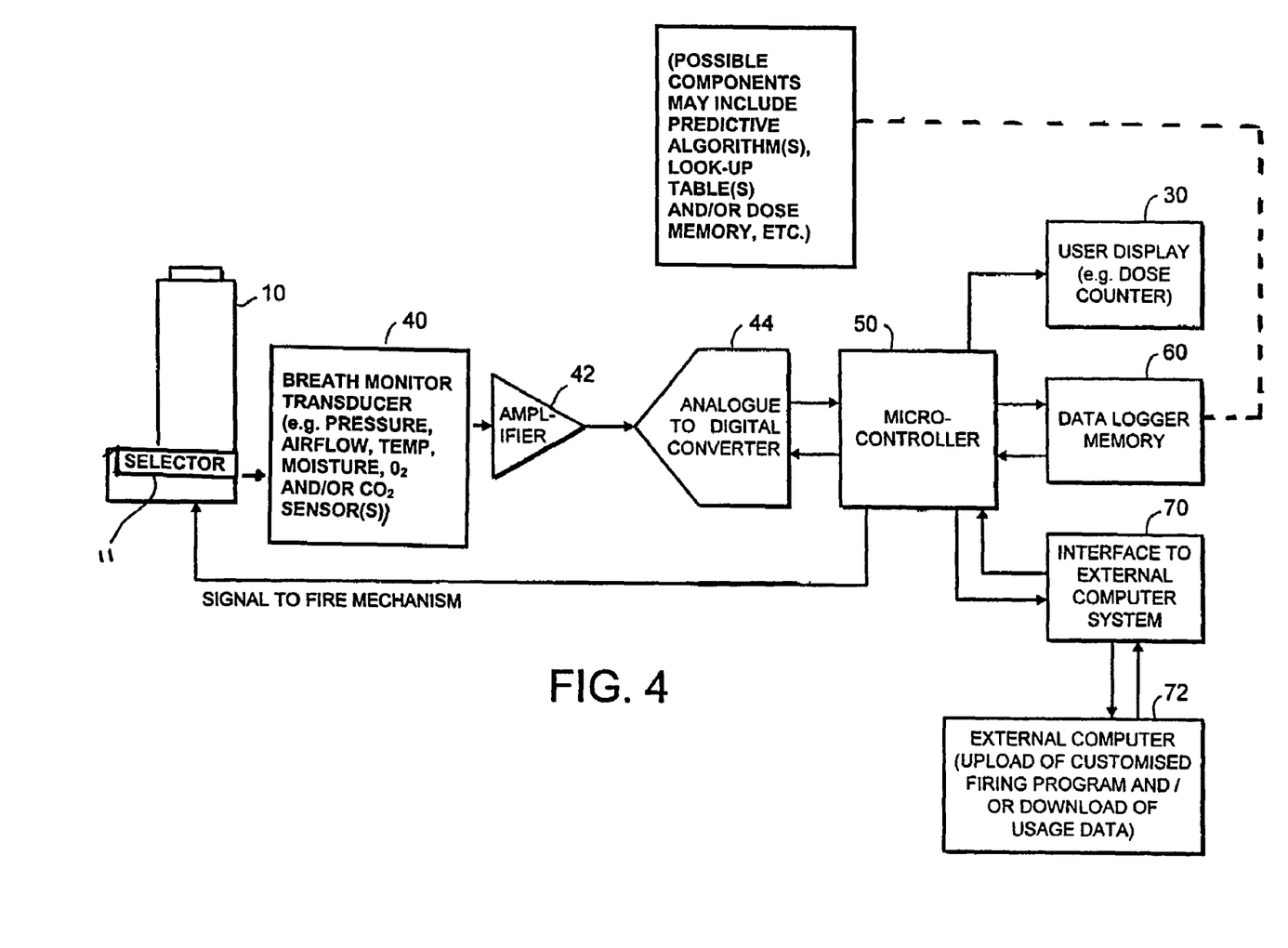
FIG. 4. is a schematic representation of a system in accord with the present invention.

FIG. 4. is a block diagram illustrating a system herein. Inhaler 10 includes breath monitor transducer 40 for sensing the pressure or flow profile through the device, thereby enabling the breathing pattern of a patient to be monitored. The breath monitor transducer 40 connects via amplifier 42 and analogue to digital converter 44 to micro-controller 50. The micro-controller 50 is for example, contained within a device attached to the inhaler 10 (as in FIG. 2.). The micro-controller 50 is in communication with a user display 30 for the visual display of information e.g. relating to number of doses dispensed. The micro-controller 50 is also in communication with a memory 60 for storage of information relating to the breathing pattern of the patient. The micro-controller 50 further communicates with an interface 70 to an external computer system 72. The external computer system 72 allows for the use of customised software such as that enabling visual display of the breathing pattern of the patient. Importantly, the micro-controller 50 also communicates with an actuator selector 11 on the inhaler 10, thereby enabling an actuation signal to be sent at the appropriate trigger point.

Figure 5:
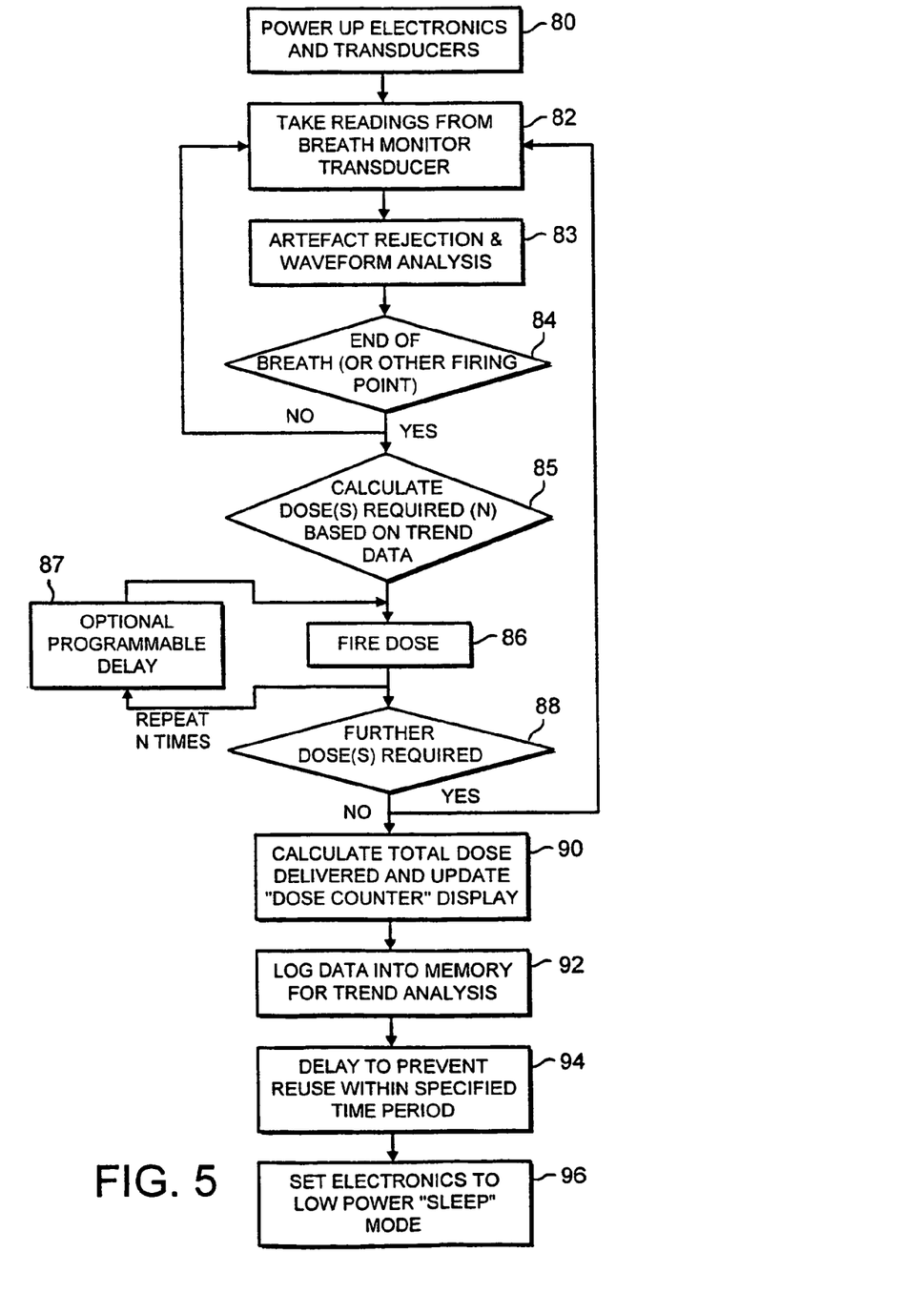
FIG. 5. is a flow-chart indicating the operation of a system in accord with the present invention.

FIG. 5. is a flow diagram illustrating a method of use of a system in accord with the invention. At point 80 the equipment is powered up, typically from a low energy 'sleep' mode. Readings from the breath monitor transducer are then taken at point 82. These readings are analysed at point 83 and corrections made for any artefacts such as if the patient coughs or takes short, sudden breaths. A picture of the patient's breathing pattern is, thus, assembled. At point 84 an assessment is made as to whether the patient is at the end of the exhalation part of the breath cycle. The trigger point is at the end of breath point, or at a point coupled thereto. At point 85 a calculation is made of the dose required. The calculation is based on trend data and on the current breathing pattern. At point 86 the dose is fired. A loop involving an optional programmable delay 87 may be included to allow for the delivery of dose by multiple, rapid firing of partial doses. At point 88 a check is made if the patient requires further doses. If further doses are required, there is a loop back to point 82.

If no further doses are required, point 90 is reached at which a calculation is made of the total dose delivered in the most recent firing pattern and the dose display is updated. Data relating to the most recent dose delivery event is logged into a memory at point 92. A delay is triggered at point 94 to prevent reuse of the system within a set time period. This delay acts as a safety mechanism. At point 96, the system is reset to the powered down 'sleep' mode.

The system of the invention is suitable for dispensing medicament, particularly for the treatment of respiratory disorders such as disorders of the lungs and bronchial tracts including asthma and chronic obstructive pulmonary disorder (COPD).

Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol, and any mixtures thereof.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). The medicaments can be in any suitable form. Preferred forms include aerosols comprising medicament suspended in a propellant with optionally one or more solvents; dry powders comprising micronized medicament and optionally one or more excipients; and solutions including aqueous solutions.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A portable, hand-held, patient-operable device for the delivery of inhalable medicament comprising:
   (a) a housing adapted to be carried by a patient breathing without the assistance of a respirator and sized to fit within the patient's hand while said device is in use by the patient;
   (b) a monitor for monitoring the breath cycle of a patient positioned within said housing;
   (c) a medicament container having a release mechanism releasing inhalable medicament therefrom; and
   (d) an actuator for actuating said release mechanism, said actuator being actuable in response to a signal from said monitor, characterized in that the monitor provides said signal at a trigger point which is correlated to the end of the exhalation part of the breath cycle.

2. A portable device according to claim 1, wherein said monitor comprises one or more sensors for sensing the pressure profile associated with the breath cycle.

3. A portable device according to claim 1, wherein said monitor comprises one or more sensors for sensing the airflow profile associated with the breath cycle.

4. A portable device according to claim 1, wherein said monitor comprises one or more sensors for sensing the temperature profile associated with the breath cycle.

5. A portable device according to claim 1, wherein said monitor comprises one or more sensors for sensing the moisture profile associated with the breath cycle.

6. A portable device according to claim 1, wherein said monitor comprises one or more sensors for sensing the oxygen or carbon dioxide profile associated with the breath cycle.

7. A portable device according to claim 1, wherein the trigger point corresponds to the point at which the lungs of the patient are most empty.

8. A portable device according to claim 1, wherein said monitor is connectable to an electronic information processor.

9. A portable device according to claim 8, wherein said electronic information processor includes an active memory for storing information about the breath cycle.

10. A portable device according to claim 9, wherein said electronic information processor includes a predictive algorithm for predicting the optimum trigger point.

11. A portable device according to claim 9, wherein said electronic information processor includes a look-up table for predicting the optimum trigger point.

12. A portable device according to claim 9, wherein said electronic information processor includes a second predictive algorithm for predicting the optimum amount of medicament to release.

13. A portable device according to claim 12, wherein said electronic information processor includes a dose memory for storing information about earlier delivered doses and reference is made to the dose memory in predicting the optimum amount of medicament to release.

14. A portable device according to claim 12, additionally comprising a display for displaying information about the optimum amount of medicament to release.

15. A portable device according to claim 12, additionally comprising a selector for selecting the amount of medicament to release.

16. A portable device according to claim 15, wherein the selector is manually operable.

17. A portable device according to claim 15, wherein the selector is operable in response to a signal from the electronic information processor.

18. A portable device according to claim 15, wherein the selector comprises a timing mechanism for varying the time interval of actuation of the actuator.

19. A portable device according to claim 15, wherein the selector comprises a metering mechanism between the container and the release mechanism for metering a variable quantity of medicament for release.

20. A portable device according to claim 15, wherein the selector comprises a multiple-fire mechanism for multiple actuation of the actuator, wherein each actuation releases a portion of the optimum amount of medicament.

21. A portable device according to claim 9, wherein said electronic information processor includes a second look-up table for predicting the optimum amount of medicament to release.

22. A portable device according to claim 1, wherein said medicament container is an aerosol container containing a medicament formulated in a pressurized liquid propellant and said release mechanism is an aerosol valve.

23. A portable device according to claim 22, wherein said aerosol valve includes a metering chamber for metering the release of medicament.

24. A portable device according to claim 23, wherein the metering chamber has a variable metering volume.

25. A portable device according to claim 24, wherein the metering chamber comprises a chamber of fixed volume which metering volume is variable by insertion of a plunger or piston.

26. A portable device according to claim 24, wherein the metering chamber is formed from an expandable material.

27. A portable device according to claim 1, wherein said medicament container is a dry-powder container or a liquid container.

28. A portable device according to claim 1, wherein said actuator comprises an energy store for storing energy which energy is releasable to activate the release mechanism of the medicament container.

29. A portable device according to claim 28, wherein said energy store comprises a biasable resilient member.

30. A portable device according to claim 28, wherein said energy store comprises a source of compressed fluid, preferably compressed gas.

31. A portable device according to claim 28, wherein said energy store comprises a chemical energy source, preferably a chemical propellant or ignition mixture.

32. A portable device according to claim 1, additionally comprising an actuation counter.

33. A portable device according to claim 1, additionally comprising a medicament release counter.

34. A portable device according to claim 1, additionally comprising a manual override.

35. An inhalation device for the delivery of inhalable medicament comprising a housing and a system according to claim 1.

36. A method for the delivery of inhalable medicament to a patient by way of a portable, handheld, patient-operable device comprising
  (i) monitoring the breath cycle of a patient by use of a monitor;
  (ii) at a trigger point, sending an actuation signal from said monitor to an actuator;
  (iii) on receipt of said actuation signal by said actuator, actuating the release of inhalable medicament to the patient,
  characterized in that said trigger point is correlated to the end of the exhalation part of the breath cycle.

37. Method according to claim 36, wherein steps (i) to (iii) are repeated until the breath cycle corresponds to a medically acceptable form.

38. Method according to claim 36, comprising
  (i) monitoring a plurality of breath cycles of a patient by use of a monitor;
  (ii) analysing said plurality of breath cycles to define an averaged breath cycle for the patient;
  (iii) predicting a trigger point from said averaged breath cycle, the trigger point being coupled to the end of the exhalation part of the averaged breath cycle;
  (iv) monitoring a further breath cycle and at said predicted trigger point sending an actuation signal from said monitor to an actuator;
  (v) on receipt of said actuation signal by said actuator, actuating the release of inhalable medicament to the patient.

* * * * *